(12) United States Patent
Campbell et al.

(10) Patent No.: US 8,119,694 B2
(45) Date of Patent: *Feb. 21, 2012

(54) HIGH CONCENTRATION LOCAL ANESTHETIC FORMULATIONS

(75) Inventors: James N. Campbell, Luthersville, MD (US); Arthur F. Michaelis, Devon, PA (US)

(73) Assignee: Arcion Therapeutics, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/542,365

(22) Filed: Aug. 17, 2009

(65) Prior Publication Data

US 2010/0041765 A1 Feb. 18, 2010

Related U.S. Application Data

(60) Provisional application No. 61/089,348, filed on Aug. 15, 2008.

(51) Int. Cl.
*A01N 37/18* (2006.01)
(52) U.S. Cl. ..................................... 514/626
(58) Field of Classification Search ................... 514/626
See application file for complete search history.

(56) References Cited

U.S. PATENT DOCUMENTS

| | | |
|---|---|---|
| 4,752,466 A | 6/1988 | Saferstein et al. |
| 4,777,046 A | 10/1988 | Iwakura et al. |
| 4,814,168 A | 3/1989 | Sablotsky et al. |
| 4,863,721 A | 9/1989 | Beck et al. |
| 4,994,267 A | 2/1991 | Sablotsky |
| 5,300,291 A | 4/1994 | Sablotsky et al. |
| 5,380,754 A | 1/1995 | Miller et al. |
| 5,411,738 A | 5/1995 | Hind |
| 5,474,783 A | 12/1995 | Miranda et al. |
| 5,589,180 A | 12/1996 | Hind |
| 5,601,838 A | 2/1997 | Hind |
| 5,656,286 A | 8/1997 | Miranda et al. |
| 5,667,799 A | 9/1997 | Caldwell et al. |
| 5,686,099 A | 11/1997 | Sablotsky et al. |
| 5,709,869 A | 1/1998 | Hind |
| 5,719,197 A | 2/1998 | Kanios et al. |
| 5,827,529 A | 10/1998 | Ono et al. |
| 5,827,829 A | 10/1998 | Hansen et al. |
| 5,948,433 A | 9/1999 | Burton et al. |
| 5,955,097 A | 9/1999 | Tapolsky et al. |
| 5,958,446 A | 9/1999 | Miranda et al. |
| 5,985,311 A | 11/1999 | Cordes et al. |
| 6,103,266 A | 8/2000 | Tapolsky et al. |
| 6,290,984 B1 | 9/2001 | Tapolsky et al. |
| 6,297,290 B2 | 10/2001 | Guise et al. |
| 6,299,902 B1 | 10/2001 | Jun et al. |
| 6,461,644 B1 | 10/2002 | Jackson et al. |
| 6,676,961 B1 | 1/2004 | Lichter |
| 6,953,590 B1 | 10/2005 | Owaki et al. |
| 7,018,647 B1 | 3/2006 | Yamasaki et al. |
| 2003/0152637 A1* | 8/2003 | Chasin et al. .................. 424/501 |
| 2004/0184994 A1 | 9/2004 | DeStefano et al. |
| 2004/0213744 A1 | 10/2004 | Lulla et al. |
| 2005/0014823 A1 | 1/2005 | Soderlund et al. |
| 2005/0090557 A1 | 4/2005 | Muhammad et al. |
| 2009/0048296 A1 | 2/2009 | Campbell et al. |

FOREIGN PATENT DOCUMENTS

| | | |
|---|---|---|
| EP | 0 043 738 | 10/1985 |
| EP | 1 293 203 | 3/2003 |
| WO | WO 93/17674 | 9/1993 |
| WO | WO 01/43722 | 6/2001 |
| WO | WO 01/54679 | 8/2001 |
| WO | WO 02/089849 | 11/2002 |
| WO | WO 2007/025142 | 3/2007 |
| WO | WO 2007/031753 | 3/2007 |

OTHER PUBLICATIONS

Williams et al. (Penetration enhancers), Advanced Drug Delivery Reviews vol. 56, Issue 5, Mar. 27, 2004, pp. 603-618.*
Brown, "MedSpray: The next generation in topical drug delivery", Drug Delivery Report Autumn/Winter, pp. 28-29 (2007).
Bupivacaine (transdermal, TRANSUR), DURECT, *Investigational Drugs Database Drug Report*, pp. 1-2, updated Feb. 6, 2008, accessed Apr. 15, 2008.
Campbell and Meyer, "Mechanisms of neuropathic pain", *Neuron*, 52(1):77-92 (2006).
Campbell, "Nerve lesions and the generation of pain", *Muscle Nerve*, 24(10):1261-73 (2001).
Cassuto, "Topical local anaesthetics and herpes simplex", *Lancet*, 1(8629):100-1 (1989).
Chabal, et al., "The use of oral mexiletine for the treatment of pain after peripheral nerve injury", *Anesthesiology*, 76(4):513-7 (1992).
Endo Pharmaceuticals Comments on Lidoderm®, http://www2.prnewswire.com/cgi-bin/stories.pl?ACCT=104&STORY=/www/story/10-17-2006/0004453647&EDATE=, pp. 1-3 (Oct. 17, 2006).
Engler, et al., "Expression of transient receptor potential vanilloid 1 (TRPV1) in synovial fibroblasts from patients with osteoarthritis and rheumatoid arthritis", *Biochem. Biophys. Res. Commun.*, 359(4):884-8 (2007). Epub Jun. 4, 2007.
Investigational Drugs Database, "lidocaine", pp. 1-2, accessed Feb. 16, 2007.
Kingery, "A critical review of controlled clinical trials for peripheral neuropathic pain and complex regional pain syndromes", *Pain*, 73(2):123-39 (1997).
Marra, et al., "Systemic toxicity from topically applied Lidocaine in conjunction with fractional photothermolysis", *Arch. Dermatol.*, 142:1024-1026 (2006).
Nakamura and Ferreira, "Peripheral analgesic action of clonidine: mediation by release of endogenous enkephalin-like substances", *Eur. Jour. Pharmacol.*, 146:223-8 (1988).
Sato and Perl, "Adrenergic excitation of cutaneous pain receptors induced by peripheral nerve injury", *Science*, 251(5000):1608-10 (1991).
Vadalouca, et al., "Therapeutic management of chronic neuropathic pain: an examination of pharmacologic treatment", *Ann. N.Y. Acad. Sci.*, 1088:164-86 (2006).

(Continued)

Primary Examiner — Sreeni Padmanabhan
Assistant Examiner — Timothy E Betton
(74) Attorney, Agent, or Firm — Pabst Patent Group LLP

(57) ABSTRACT

A transdermal topical anesthetic formulation, which can be used to ameliorate or inhibit pain, has been developed. In the preferred embodiment, the topical anesthetic is a local anesthetic such as lidocaine, most preferably lidocaine free-base in a gel, and the dosage of the local anesthetic is effective in the painful area or immediately adjacent areas, to ameliorate or eliminate the pain. High concentration of local anesthetic in solution in the carrier is used to drive rapid release and uptake of the drug. Relief is typically obtained for a period of several hours.

24 Claims, 4 Drawing Sheets

OTHER PUBLICATIONS

Yanagi, et al. "Destabilization of herpes simplex virus type 1 virions by local anesthetics, alkaline pH, and calcium depletion", *Arch. Virol.*, 108(1-2):151-9 (1989).

Arpey, et al., "Advances in local anesthesia," *Clin. Dermatol.*, 10(3):275-83 (1992).

Bagesund, et al., "Lidocaine 20% patch vs lidocaine 5% gel for topical anaesthesia of oral mucosa," *Int. J. Paediatr, Dent.*, 18(6):452-60 (2008).

Chemische Fabrik Kreussler and Co GmbH, "Dynexan Mundgel," http://www.ernsite.de/de/dynexan_mundgel.html (accessed Dec. 11, 2009).

Eidelman, et al., "Topical anesthetics for dermal instrumentation: a systematic review of randomized, controlled trials," *Ann. Emerg. Med.*, 46(4):343-51 (2005).

Galer, et al., "Lidocaine patch 5% improves outcomes for low-back pain and osteoarthritis patients receiving COX-2-selective or traditional NSAID therapy for pain relief," *J. Pain*, 6(3):S50 (2005).

Galer, et al., "A randomized, open-label study comparing the efficacy and safety of lidocaine patch 5% with celecoxib 200 mg in patients with pain from osteoarthritis of the knee," *J. Pain*, 6(3):S51 (2005).

Kasaj, et al., "Effectiveness of a topical salve (Dynexan) on pain sensitivity and early would healing following nonsurgical periodontal therapy," *Eur. J. Med. Res.*, 12(5):196-9 (2007).

* cited by examiner ns" by James N. Campbell, filed in the United States Patent
HIGH CONCENTRATION LOCAL ANESTHETIC FORMULATIONS

CROSS REFERENCE TO RELATED APPLICATIONS

This application claims benefit to U.S. Ser. No. 61/089,348 entitled "High Concentration Local Anesthetic Formulations" by James N. Campbell, filed in the United States Patent and Trademark office on Aug. 15, 2008.

TECHNICAL FIELD

The present invention relates to formulations containing a high concentration of topical anesthetic, such as lidocaine, which can be used for the treatment of pain.

BACKGROUND OF THE INVENTION

Classic analgesics have limited utility because of lack of efficacy or a high incidence of side effects. Data from clinical studies and conventional clinical wisdom indicate that NSAIDs are poorly effective. Opioids may be effective but side effects, tolerance, concern about addiction and diversion all limit their utility. A review analyzing the controlled clinical data for peripheral neuropathic pain (PNP) (Kingery, Pain, 73(2):123-39 (1997) reported that NSAIDs were probably ineffective as analgesics for PNP and that there was no long-term data supporting the analgesic effectiveness of any drug. The results of published trials and clinical experience provide the foundation for specific recommendations for first-line treatments, which include gabapentin, 5% lidocaine patch, opioid analgesics, tramadol hydrochloride, and tricyclic antidepressants (reviewed by Vadalouca, et al., Ann NY Acad. Sci., 1088:164-86 (2006).

Delivery of drugs by the transdermal route has been known for many years. Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Methods for making transdermal patches are described in U.S. Pat. Nos. 6,461,644, 6,676,961, 5,985,311, 5,948,433. Lidocaine-containing formulations are described in U.S. Pat. Nos. 4,777,046, 5,958,446, 5,719,197, 5,686,099, 5,656,286, 5,474,783, 5,300,291, 4,994,267, 4,814,168, 7,018,647, 6,299,902; and 6,297,290. U.S. Patent Application No. 2009/0048296 describes formulations containing a high concentration of lidocaine in the range of at least 20%, preferably about 40%.

Topical gels, plasters, and patches are described in U.S. Pat. Nos. 5,411,738, 5,601,838, 5,709,869 and 5,827,829 which are assigned to Endo Pharmaceuticals. The gels described in these patents contain from 2-20% lidocaine, preferably from 1-10% or 5-10% lidocaine.

A 5% lidocaine patch marketed as LIDODERM® is available from Endo Pharmaceuticals, Inc. The LIDODERM® patch comprises an adhesive material containing 5% lidocaine, which is applied to a non-woven polyester felt backing and covered with a polyethylene terephthalate (PET) film release liner. This patch is applied only once for up to 12 hours in a given 24 hour period. The marketed patch provides satisfactory therapy to some patients. Delivery of lidocaine in a patch, however, has numerous liabilities for the patient. Since the patch is a finite size and shape, the application area is determined by the patch and not by the dimensions of the painful site. If the area of pain is other than a large smooth surface, the patch may not necessarily fit the area or be comfortable to the wearer since the patch may not conform to the defect. For example, the patch is difficult to apply to toes and fingers. Applying the patch to the face creates a stigma issue for patients. The patch is undesirable for hair bearing areas as well since hair limits adhesiveness and because of the depilitation that may occur with removal of the patch. The patch may also make the patient warmer, and thus be a burden in hot environments.

The delivery of drug from the lidocaine patch is designed to be constant over the 12-hour exposure period. However, it may be therapeutically important to provide a loading dose of drug to eliminate pain quickly when first administering the therapy. It is well known in the treatment of pain that more analgesic is required to treat established pain than is needed to prevent pain from becoming more intense. Such a profile cannot be provided by a patch delivering at a constant rate.

It is therefore an object of the present invention to provide topical anesthetic formulations that can be used to provide relief from pain over a period of time.

SUMMARY OF THE INVENTION

A topical anesthetic formulation containing a high concentration of local anesthetic in a pharmaceutically acceptable carrier for topical application and method of use to ameliorate or inhibit pain, including neuropathic pain, has been developed, such that the target tissue (skin) is appropriately dosed with anesthetic. In one embodiment, the formulation is used to treat pain other than neuropathic pain. In the preferred embodiment, the local anesthetic is lidocaine, most preferably lidocaine free base, most preferably in a continuous phase gel, although creams, lotions, foams, sprays or ointments may also be used, and the dosage of the local anesthetic is effective in the painful area or immediately adjacent areas, to ameliorate or eliminate the pain. The formulations may release the largest dose of drug shortly after administration, for example, from 0 up to and including about 12 hours after administration, preferably from 0 to 8 hours. In another embodiment, the formulation releases the largest dose of drug from 0 to 6 hours. In a particular embodiment, the formulation provides an initial burst release within two hours. In another particular embodiment, the formulation provides an initial burst release within four hours. In still another particular embodiment, the formulation provides an initial burst release within six hours, and in still another particular embodiment, the formulation provides an initial burst release at about 8 hours. Earlier time period release may result in a more rapid onset of pain relief for the patient.

The concentration of the drug in the formulation is from about greater than 20% to about 40% or higher by weight of the formulation. In the preferred embodiment, the concentration is about 40%.

The formulation is applied to the site of, or adjacent to, the painful area. Relief is typically obtained for a period of several hours or days, depending on the dosing schedule. The formulations can be applied once a day or more frequently, such as two times or three times a day.

The preparation may be used for local topical delivery to any location where reduction of pain is required or desirable. This would apply to wounds, burns, and areas where medical procedure and cosmetic procedures are done. For example it would be desirable to use a rapidly acting anesthetic in a location where a patient has an abrasion or other skin wound that causes pain. Burns cause pain and it would be desirable to reduce pain quickly by local application of an anesthetic.

Pain also is frequently associated with medical and cosmetic procedures. This would apply to locations where a needle is injected into the skin for example to start an IV or draw blood or inject medicines into a reservoir implanted under the skin. Depillitation, and laser resurfacing are examples of cosmetic painful procedures, and application of a rapidly acting local anesthetic may reduce pain by being applied just before the procedure.

A single dose irritation/pharmacokinetics study was conducted with White New Zealand Rabbits. $AUC_{0-t}$ increased disproportionately in male and female rabbits when the dermal dose was increased from 30 to 300 mg/kg when lidocaine was delivered using either the ARC-31 or ARC-32 lidocaine gel, 40% formulation. It increased 1.7- to two-fold in male and female rabbits when the dose of the ARC-31 gel was increased to 1000 mg/kg. $C_{max}$ increased approximately 7- to 19-fold when the dose increased from 30 to 300 mg/kg using either gel. The median $T_{max}$ of lidocaine was 8 hours when the rabbits were dosed with the ARC-31 lidocaine gel; it decreased to 1 hour when the ARC-32 lidocaine gel was used.

The mean values of $C_{max}$ and $AUC_{0-t}$ of lidocaine between male and female animals were either comparable when the ARC-31 gel was dosed or 42-50% higher in males when the ARC-32 gel was administered.

Exposure to lidocaine, as measured using both $C_{max}$ and $AUC_{0-t}$, was greater in rabbits dosed using the ARC-32 lidocaine gel compared to the ARC-31 lidocaine gel.

BRIEF DESCRIPTION OF THE DRAWINGS

FIG. 2 is a graph showing the mean plasma concentration of lidocaine (ng/ml) in White New Zealand Rats administered dermally ARC-31 Lidocaine Gel, 40% at a dose of 30 mg/kg (■), 300 mg/kg (▲), and 1000 mg/kg (●) as a function of time (hours) post dose.

FIG. 3 is a graph showing the mean plasma concentration of lidocaine (ng/ml) in White New Zealand Rats administered dermally ARC-32 Lidocaine Gel, 40% at a dose of 30 mg/kg (■) and 300 mg/kg (▲) as a function of time (hours) post dose.

DETAILED DESCRIPTION OF THE INVENTION

I. Formulations

Figure 1:
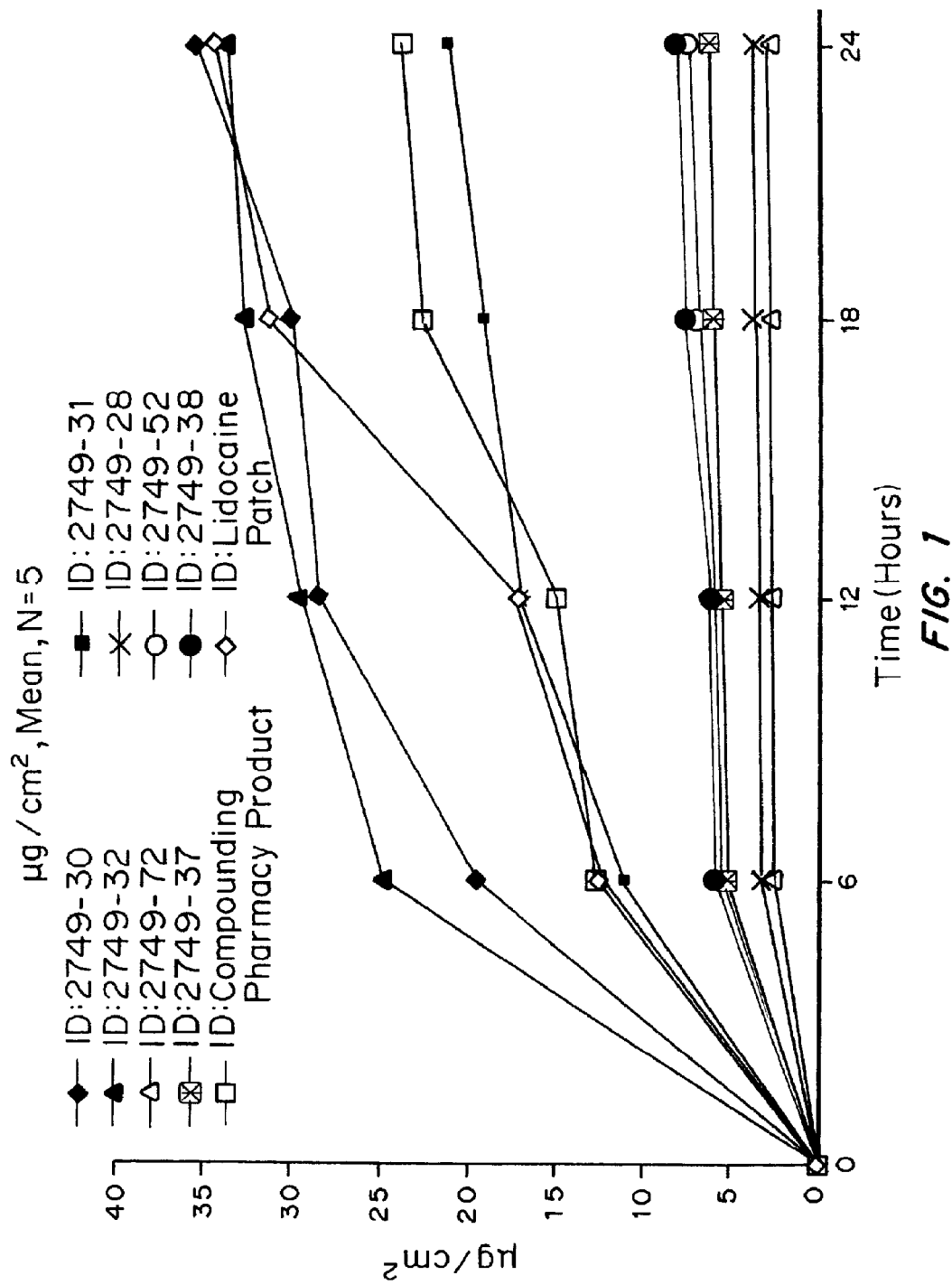
FIG. 1 is a graph of the cumulative penetration of lidocaine from: gels ID: 2749-30 (♦), ID: 2749-32 (σ), ID: 2749-31 (v), and ID: 2749-28 (lidocaine HCl, X); spray ID: 2749-72 (☉); creams ID: 2749-38 (λ) and ID: 2749-37 (*); foam ID: 2749-52 (λ); compounding pharmacy product (∀); and a lidocaine patch (❧) through human skin, measured as micrograms lidocaine/cm$^2$, over time in hours.

The formulations contain high concentrations of drug applied in a continuous phase directly to the surface of affected skin. "High concentration", as used herein, means that release of the drug is governed by the Second Law of thermodynamics; rather than Fick's Second Law of Diffusion, which governs the release of drug from dilute solutions. Fick's Second Law of diffusion instructs the rate of release drug from dilute solutions. The result is that a large dose of drug is released in the early time period following administration, for example, 0-12 hours following administration. The formulations may release the largest dose of drug shortly after administration, for example, from 0 up to and including about 12 hours after administration, preferably from 0 to 8 hours. In another embodiment, the formulation releases the largest dose of drug from 0 to 6 hours. In a particular embodiment, the formulation provides an initial burst release within two hours. In another particular embodiment, the formulation provides an initial burst release within four hours. In still another particular embodiment, the formulation provides an initial burst release within six hours, and in still another particular embodiment, the formulation provides an initial burst release at about 8 hours. Earlier time period release may result in a more rapid onset of pain relief for the patient.

"High concentration" will typically be a concentration of greater than 20% drug/carrier w/w, as discussed in more detail below.

The formulation may be a single-phase system such as a gel or a more complex multiphasic system wherein one or more additional phases may be in dynamic equilibrium with the continuous phase. Examples of such systems include creams, lotions, emulsions of lipid containing droplets throughout a continuous aqueous phase, stable micellar dispersions, combinations of an emulsion with excess drug particles distributed throughout, and self-emulsifying systems. The common attribute of the various formulations would be the very high concentration of the drug in the continuous phase of the system.

As discussed above, Fick's Second Law of Diffusion governs release of drug from dilute solutions. However, Fick's law breaks down in very highly concentrated solution. In very highly concentrated solutions, the presence of the solute (i.e., drug) inhibits the ability of the solvent molecules to orient at will. Solvation of the drug in these highly concentrated solutions causes specific orientation of adjacent water molecules to a very high degree, creating a very high-energy state. Since the Second Law of Thermodynamics instructs that molecules will always seek a state of increased entropy in order to lower the overall energy of the system, there is an enhanced thermodynamic driving force to force the drug out of the continuous phase and across the barrier membranes of the skin. Removal of the drug from the continuous phase results in an increase in the entropy of the continuous phase as lowering concentration of the drug allows for more movement of the solvent molecules (i.e., increase in entropy) and, thus, an overall decrease in the energy of the system. The result is rapid early time delivery of the drug from the drug product to the target tissues.

Evidence of this effect can be seen in the data in the examples. In one embodiment, a highly concentrated gel formulation provided higher early time (e.g. first six hours)

levels of drug transport across the human skin membranes than does the reference lidocaine patch (5% drug content) or the lidocaine hydrochloride creams which have only very low effective levels of lidocaine free base (the uncharged base can cross the barrier membranes whereas the charged salt form can not) (see the Examples). In another embodiment, a highly concentrated gel formulation exhibited a nearly identical level of drug transport across the human skin membranes compared to the reference lidocaine patch (5% drug content) (see the Examples).

A. Local Anesthetics

As used herein, the term "local anesthetic" means a drug which provides local numbness or pain relief. Local anesthetics cause reversible blockage of conduction and/or initiation of action potentials typically by actions related to the interference with voltage gated sodium channels. Lipid solubility appears to be the primary determinant of intrinsic anesthetic potency. Chemical compounds which are highly lipophilic tend to penetrate the nerve membrane more easily, such that fewer molecules are required for conduction blockade resulting in enhanced potency.

Chemically most local anesthetics are esters or amides. Esters include, but are not limited to, procaine, tetracaine, and chloroprocaine. They are hydrolyzed in plasma by pseudocholinesterase. Amides include, but are not limited to, lidocaine, mepivicaine, prilocaine, bupivacaine, and etidocaine. These compounds are often referred to as the "caine alkaloids". Caine alkaloids generally have high first pass metabolisms. The liver rapidly metabolizes the drug and the kidneys excrete the metabolites and/or unchanged drug.

A number of different local anesthetics can be used, including dibucaine, bupivacaine, etidocaine, tetracaine, lidocaine, and xylocaine. In the preferred embodiment, the anesthetic is lidocaine, most preferably in the form of the free base, although it may be possible to use a salt, for example, the hydrochloride, hydrobromide, acetate, citrate, or sulfate salt. As demonstrated in the examples, gels containing lidocaine free base and creams and sprays containing lidocaine HCl were prepared. Compared to the free base form of these drugs, the more hydrophilic hydrochloride salt displays longer and denser nerve block, more complete release from matrices, slower clearance from the targeted nerve area, and less encapsulation.

The formulations described herein should deliver a high local concentration with little systemic absorption, which should minimize the adverse side effects associated with the systemic absorption of caine alkaloids. For example, after administration of formulations containing lidocaine free base, little or no unchanged drug was detected in the plasma.

The formulations contain from greater than about 20% to about 60% of the drug by weight of the formulation. In the preferred formulation, the formulation contains about 40% by weight of lidocaine, most preferably of the free base. More of the salt form is required to achieve the same transdermal uptake, based on the studies in the following examples. The concentration and pharmacokinetics are dependent on the form of the local anesthetic and the excipient, as discussed in more detail below and demonstrated by the examples. In general, a lower concentration of lidocaine free base in a gel will provide equivalent uptake as a higher concentration of lidocaine HCl in a multiphasic excipient.

B. Excipients

1. Lotions, Creams, Gels, Ointments, Foams

"Water Soluble" as used herein refers to substances that have a solubility of greater than or equal to 5 g/100 ml water.

"Lipid Soluble" as used herein refers to substances that have a solubility of greater than or equal to 5 g/100 ml in a hydrophobic liquid such as castor oil.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexyl stearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol.

The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes. Self generating emulsions are known to enhance the absorption of drugs as shown in the following table.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%. Examples of the composition of lidocaine/lidocaine hydrochloride creams are shown in the examples.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Examples of the composition of lidocaine/lidocaine hydrochloride gels are shown in the examples. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

II. Methods of Treatment

A. Effective Dosages; Sites of Administration

The formulations described herein can be administered at or adjacent to the sites of pain to provide relief. The formulations can be administered once a day, for example, for fast, temporary pain relief or more frequently, such as twice or three times a day, to maintain pain relief over an extended period of time.

1. Topical

The composition is applied topically to a site at or adjacent to a painful region. The composition is reapplied as necessary. The dosing is applied to the painful skin and subcutaneous structures in order to effect pain relief while avoiding the side effects associated with systemic delivery. Pain relief is obtained within minutes to hours and lasts for periods of approximately three to six hours to 24 hours. The compounds are applied such that the dosage is sufficient to provide an effective dose in the painful area or immediately adjacent areas, to ameliorate or eliminate pain and other unpleasant sensations such as itching.

The formulations may release the largest dose of drug shortly after administration, for example, from 0 up to and including about 12 hours after administration, preferably from 0 to 8 hours. In another embodiment, the formulation releases the largest dose of drug from 0 to 6 hours. In a particular embodiment, the formulation provides an initial burst release within two hours. In another particular embodiment, the formulation provides an initial burst release within four hours. In still another particular embodiment, the formulation provides an initial burst release within six hours, and in still another particular embodiment, the formulation provides an initial burst release at about 8 hours. Earlier time period release may result in a more rapid onset of pain relief for the patient.

A single dose irritation/pharmacokinetics study was conducted with White New Zealand Rabbits. $AUC_{0-t}$ increased disproportionately in male and female rabbits when the dermal dose was increased from 30 to 300 mg/kg when lidocaine was delivered using either the ARC-31 or ARC-32 lidocaine gel, 40% formulation. It increased 1.7- to two-fold in male and female rabbits when the dose of the ARC-31 gel was increased to 1000 mg/kg. Cmax increased approximately 7- to 19-fold when the dose increased from 30 to 300 mg/kg using either gel. The median $T_{max}$ of lidocaine was 8 hours when the rabbits were dosed with the ARC-31 lidocaine gel; it decreased to 1 hour when the ARC-32 lidocaine gel was used.

The mean values of $C_{max}$ and $AUC_{0-t}$ of lidocaine between male and female animals were either comparable when the ARC-31 gel was dosed or 42-50% higher in males when the ARC-32 gel was administered. Exposure to lidocaine, as measured using both Cmax and AUC0-t, was greater in rabbits dosed using the ARC-32 lidocaine gel compared to the ARC-31 lidocaine gel.

2. Intradermal

Some of the formulation can be administered intradermally, using, for example, an insulin syringe. Care should be taken to administer the smallest dose possible, and in all cases, topical or intradermal, care should be taken to avoid systemic levels or local toxicity.

B. Therapeutic Indications

The preparation may be used for local topical delivery to any location where reduction of pain is required or desirable. In one embodiment, the formulations are used to treat pain, other than neuropathic pain. This would apply to pain cause by injuries, such as wounds and burns, and areas where medical procedure and cosmetic procedures are done. For example it would be desirable to use a rapidly acting anesthetic in a location where a patient has an abrasion, cut, puncture wound or other skin wound that causes pain. Burns cause pain and it would be desirable to reduce pain quickly through application of a rapidly acting local anesthetic.

Pain also is frequently associated with medical and cosmetic procedures. For example, this would apply to locations where a needle is injected into the skin for example to start an IV or draw blood or inject medicines into a reservoir implanted under the skin. Depillitation, and laser resurfacing are examples of cosmetic painful procedures, and application of a rapidly acting local anesthetic may reduce pain by being applied just before the procedure.

III. Kits

Kits containing formulations from greater than about 20% to about 60% of the drug by weight of the formulation are described herein. In one embodiment, the formulation contains about 40% by weight of lidocaine, in the form of the free base or a pharmaceutically acceptable salt. In a preferred embodiment, the drug is in the form of the free base. The kit may include a container containing the formulation, for example, in the form of a lotion, cream, ointment, gel, or foam. The kit may further contain instructions for administering the formulation as well as medical devices or supplies for administering the formulation, such as gloves, applicators, such as a q-tip or swab, and combinations thereof.

EXAMPLES

The present invention will be further understood by reference to the following non-limiting examples.

Example 1

Determination of Solubility and Compatibility of Lidocaine and Lidocaine HCl in Pharmaceutically Acceptable Topical Carrier The primary goal was to develop a fast-acting topical product containing 40% Lidocaine as the Active Pharmaceutical Ingredient (API) with limited systemic exposure for the treatment of neuropathic pain.

Materials and Methods

The solubility and compatibility of lidocaine and lidocaine HCl in solvents typically used in topical pharmaceutical products was assessed in order to direct the formulation development efforts. The solvents were selected based on anticipated solubility parameters and solvent behavior, and their inclusion on the FDA approved Inactive Ingredient Guide (IIG). Additional attributes included the ability to accommodate a high level of drug while retaining adequate cosmetic properties, and the potential for a quick-drying product for application to the torso and face.

Initially, the solubility of lidocaine and lidocaine hydrochloride was evaluated in single solvents with varying lipophilicity. Given the high concentration of API, the solubilized drug samples were visually inspected following a week of storage to ensure no crystallization had occurred. Based on the single solvent data, a compatibility study was initiated to evaluate the chemical stability of the drug at a concentration of 40% w/w in a variety of solvent blends that would form the base of potential prototype gel or cream formulations. Both lidocaine and lidocaine hydrochloride retained their physical appearance and the absence of a drop in potency between the two week samples stored at accelerated conditions versus the initial samples supported the chemical compatibility of lidocaine in the solvent blends.

TABLE 1

R&D Stability Summary

| Batch # (type) | T₀ | Conditions | pH | Assay (API % LC) | Viscosity (cP) | Comment |
|---|---|---|---|---|---|---|
| 2749-28 (Lidocaine HCl gel) | pH = 5.54 Assay = 99.6 Viscosity = ND | Freeze/thaw | 5.78 | 104.4 | ND | |
| | | Hot/cold | 5.69 | 105.6 | ND | |
| | | 1 month @ 5° C. | 5.82 | 103.3 | ND | |
| | | 1 month @ 25° C. | 5.80 | 104.8 | ND | |
| | | 1 month @ 40° C. | 5.77 | 104.6 | ND | |
| | | 3 months @ 5° C. | 5.54 | 102.4 | ND | |
| | | 3 months @ 25° C. | 5.62 | 102.9 | 5400** | |
| | | 3 months @ 40° C. | 5.71 | 102.9 | ND | |
| 2749-30 (Lidocaine gel) | pH = 9.35 (1:9) Assay = 104.2 Viscosity = ND | Freeze/thaw | 8.75 (1:9) | 102.7 | ND | |
| | | Hot/cold | 8.97 (1:9) | 105.8 | ND | |
| | | 1 month @ 5° C. | 8.91 (1:9) | 104.5 | ND | |
| | | 1 month @ 25° C. | 8.79 (1:9) | 102.6 | ND | |
| | | 1 month @ 40° C. | 8.81 (1:9) | 102.9 | ND | |
| | | 3 months @ 5° C. | ND | 105.1 | ND | |
| | | 3 months @ 25° C. | 9.43 (1:9) | 105.4 | 3750* | |
| | | 3 months @ 40° C. | ND | 102.4 | ND | |
| 2749-31 (Lidocaine gel) | pH = 9.40 (1:9) Assay = 99.2 Viscosity = ND | Freeze/thaw | 9.13 (1:9) | 101.8 | ND | |
| | | Hot/cold | 9.15 (1:9) | 104.3 | ND | |
| | | 1 month @ 5° C. | 9.20 (1:9) | 100.5 | ND | |
| | | 1 month @ 25° C. | 9.22 (1:9) | 102.8 | ND | |
| | | 1 month @ 40° C. | 9.26 (1:9) | 101.0 | ND | |
| | | 3 months @ 5° C. | ND | 103.4 | ND | |
| | | 3 months @ 25° C. | 9.70 (1:9) | 99.7 | 4375* | |
| | | 3 months @ 40° C. | ND | 100.6 | ND | |
| 2749-32 (Lidocaine gel) | pH = 9.40 (1:9) Assay = 99.8 Viscosity = ND | Freeze/thaw | 9.13 (1:9) | 104.5 | ND | |
| | | Hot/cold | 9.15 (1:9) | 101.3 | ND | |
| | | 1 month @ 5° C. | 9.20 (1:9) | 101.3 | ND | |
| | | 1 month @ 25° C. | 9.22 (1:9) | 101.0 | ND | |
| | | 1 month @ 40° C. | 9.26 (1:9) | 100.8 | ND | |
| | | 3 months @ 5° C. | ND | 103.4 | ND | |
| | | 3 months @ 25° C. | 9.70 (1:9) | 102.5 | 3650* | |
| | | 3 months@40° C. | ND | 101.7 | ND | |
| 2749-37 (Lidocaine HCl Cream) | pH = 5.55 Assay = 101.2 Viscosity = 2,658** (60 rpm) | Freeze/thaw | 5.87 | 104.6 | 3095** | |
| | | Hot/cold | 6.02 | 102.8 | 3079** | |
| | | 1 month @ 5° C. | 6.06 | 105.1 | ND | |
| | | 1 month @ 25° C. | 6.06 | 104.2 | ND | |
| | | 1 month @ 40° C. | 6.08 | 104.7 | ND | |
| | | 3 months @ 5° C. | ND | 99.6 | ND | Phase separation |
| | | 3 months @ 25° C. | 5.98 | 104.6 | 3300* | |
| | | 3 months @ 40° C. | 5.90 | 104.0 | ND | |
| 2749-38 (Lidocaine HCl Cream) | pH = 5.60 Assay = 99.1 Viscosity = ND | Freeze/thaw | 6.02 | 100.2 | ND | |
| | | Hot/cold | 6.01 | 102.5 | ND | |
| | | 1 month @ 5° C. | 6.04 | 108.3 | ND | |
| | | 1 month @ 25° C. | 6.07 | 101.8 | ND | |
| | | 1 month @ 40° C. | 6.08 | 101.4 | ND | |
| | | 3 months @ 5° C. | ND | 100.7 | ND | Phase separation |
| | | 3 months @ 25° C. | 5.92 | 101.0 | 2225* | |
| | | 3 months @ 40° C. | 5.90 | 103.0 | ND | |
| 2749-42 (Lidocaine HCl Spray) | pH = 5.54 Assay = ND Viscosity = ND | Freeze/thaw | 5.13 | 99.2 | ND | |
| | | Hot/cold | 5.20 | 99.7 | ND | |
| | | 1 month @ 5° C. | 5.17 | 99.6 | ND | |
| | | 1 month @ 25° C. | 5.23 | 100.6 | ND | |
| | | 2.5 months @ 40° C. | 5.26 | 99.8 | ND | |
| | | 3 months @ 5° C. | 5.52 | 103.2 | ND | |
| | | 2.5 months @ 25° C. | 5.50 | 100.6 | ND | |
| | | 2.5 months @ 40° C. | 5.41 | 103.3 | ND | |

TABLE 1-continued

R&D Stability Summary

| Batch # (type) | T$_0$ | Conditions | pH | Assay (API % LC) | Viscosity (cP) | Comment |
|---|---|---|---|---|---|---|
| 2749-52 Lidocaine HCl Foam) | pH = 5.63 Assay = ND Viscosity = ND | Freeze/thaw | 5.20 | 102.8 | ND | |
| | | Hot/cold | 5.22 | 101.0 | ND | |
| | | 1 month @ 5° C. | 5.21 | 101.4 | ND | |
| | | 1 month @ 25° C. | 5.22 | 101.7 | ND | |
| | | 1 month @ 40° C. | 5.20 | 102.0 | ND | |
| | | 2.5 months @ 5° C. | 5.442 | 104.3 | ND | |
| | | 2.5 months @ 25° C. | 5.50 | 101.3 | ND | |
| | | 2.5 months @ 40° C. | 5.53 | 102.7 | ND | |

TABLE 2A

Composition of creams with Lidocaine HCl as the active agent;
Compositions of creams with lidocaine as the active agent

| Ingredients | IIG Max. | Wt % Batch #9 | Wt % Batch #10 | Wt % Batch #11 | Function |
|---|---|---|---|---|---|
| Lidocaine HCL | N/A | 40 | 40 | 40 | Active |
| Propylene glycol | 98 | 5.0 | 5.0 | 5.0 | Solvent/Delivery Agent |
| Glycerin | 50 | — | — | 3.0 | Humectant |
| Water | N/A | qs(43.5) | qs(43.5) | qs(38.1) | Solvent |
| Hydroxyethylcellulose250-HHA-Pharm | 4.0 | 1.0 | 1.0 | 1.0 | Gelling Agent |
| Diisopropyl adipate | 20 | — | 10 | — | Oil Phase |
| Oleyl alcohol | 10 | — | — | 5.0 | Oil Phase |
| Light Mineral oil | 95 | 10 | — | 7.0 | Oil Phase |
| Pemulen TR1 (Carbomer 1342) | 0.3 | 0.3 | 0.3 | 0.3 | Emulsifier |
| Span 80 (Sorbitan monooleate) | 7.0 | — | — | 0.4 | Emulsifier |
| Methylparaben | 70.0 | 0.17 | 0.17 | 0.17 | Preservative |
| Propylparaben | 30.0 | 0.03 | 0.03 | 0.03 | Preservative |

| Ingredients | IIG Max. | Wt % Batch #5 | Wt % Batch #6 | Function |
|---|---|---|---|---|
| Lidocaine | N/A | 40 | 40 | Active |
| Isopropyl myristate | 35 | 10.0 | 10 | Solvent/Emollient |
| Diisopropyl adipate | 20 | 10 | — | Solvent/Delivery Agent |
| Myristyl lactate | 92 | qs(18.1) | qs(21.1) | Solvent/Delivery Agent |
| Oleic acid | 7.4 | — | 7 | Solvent/Delivery Agent |
| Hydroxypropyl cellulose, HSV Pharm | 4.0 | 1.0 | 1.0 | Gelling Agent |
| Pemulen TR2 (Carbomer 1342) | 0.3 | 0.3 | 0.3 | Emulsifier |
| Polysorbate 80 (Tween 80) | 9.4 | 0.4 | 0.4 | Emulsifier |
| Methylparaben | 70.0 | 0.17 | 0.17 | Preservative |
| Propylparaben | 30.0 | 0.03 | 0.03 | Preservative |
| Propylene glycol | 98 | 1.0 | 1.0 | Solvent |
| Water | N/A | 19 | 19 | Vehicle |

TABLE 2B

Composition of gels with Lidocaine HCl as the active agent;
Composition of gels with Lidocaine as the active agent

| Ingredients | IIG Max. | Wt % Batch #7 | Wt % Batch #8 | Function |
|---|---|---|---|---|
| Lidocaine HCL | N/A | 40 | 40 | Active |
| Benzyl alcohol | 50 | 2 | 2 | Preservative |

TABLE 2B-continued

Composition of gels with Lidocaine HCl as the active agent;
Composition of gels with Lidocaine as the active agent

| | | | | | |
|---|---|---|---|---|---|
| Propylene glycol | 98 | 5 | 10 | | Solvent/Delivery Agent |
| Glycerin | 50 | 3 | — | | Humectant |
| Sorbitol, 70% | 67.52 | — | 3 | | Humectant |
| Isopropyl alcohol | 99 | — | 10 | | Solvent |
| Water | N/A | qs(49) | qs(34) | | Solvent |
| Hydroxyethyl cellulose, 250-HHX-Pharm | 1.25 | 1.0 | 1.0 | | Gelling Agent |

| | | Wt % | | | | |
|---|---|---|---|---|---|---|
| Ingredients | II Max. | Batch #1 | Batch #2 | Batch #3 | Batch #4 | Function |
| Lidocaine | N/A | 40 | 40 | 40 | 40 | Active |
| Isopropyl myristate | 35 | — | — | — | 10 | Solvent/Emollient |
| TRANSCUTOL® P (Diethylene Glycol Monoethyl Ether) | 25 | 10 | 10 | 20 | 10 | Solvent/Emollient |
| Propylene glycol | 98 | 20 | 10 | 10 | 20 | Solvent/Emollient |
| Dimethyl isosorbide | 15 | — | 10 | 10 | — | Solvent/Emollient |
| Ethyl acetate | 31 | — | 10 | — | — | Solvent/Emollient |
| Isopropyl alcohol | 99 | qs(18.8) | qs(18.8) | — | — | Solvent |
| Ethanol | 96 | — | — | qs(18.8) | qs(18.8) | Solvent |
| Water (purified) | N/A | 10.0 | | | | Vehicle |

A total of eleven formulations were prepared in which lidocaine or lidocaine hydrochloride was formulated at 40% w/w, shown in Tables 2A and 2B. Out of the 11 formulations, four contained the lidocaine free base (both non-aqueous and aqueous gels), while the remaining seven formulations contained the HCl salt form of lidocaine (cream, gel, spray, and foam dosage forms). The formulations were packaged in clear glass vials and stored at 5° C., 25° C., and 40° C. for a month. Separately, they were also subjected to three cycles each of freeze/thaw or hot/cold temperature cycling.

All prototype formulations were tested for potency of the active, appearance, and pH. Select samples were also submitted for viscosity and microscopy testing.

Results

Stability results are shown in Table 1.

The data show no significant loss of the active with time or temperature for all prototype formulations tested. No evidence of degradation products was observed.

None of the prototypes showed a change in appearance at any of the conditions tested with the exception of 2749-37 and 2749-38 which exhibited phase-separation when stored at 5° C. Prototype formulations containing the lidocaine base showed an increase in color (yellowish) intensity with an increase in storage temperature. Formulation 2749-30 had a strong odor, which can be attributed to the ethyl acetate it contains.

After storage for three months at 25° C., no precipitation or crystallization was observed. The pH values for the prototype formulations, with the exception of the gels listed below, ranged form 5.41 to 5.98. Target pH was 5.5 to 6.0. The measured pH represents no significant change from the initial value for all samples evaluated. Prototype gels containing lidocaine (2749-30 and 2749-32) are non-aqueous; therefore pH was measured following a 1:9 dilution with water in order to monitor changes to the pH of the diluted composition. The data show no significant change in measured pH value with time or temperature.

Select samples were evaluated for viscosity. None showed noticeable thinning and all samples maintained their gel-like or creamy consistency. Prototype 2749-28 exhibited some stringiness, which could be optimized by varying the concentration of the thickening agent in the product.

In summary, after one month of storage, the formulations were physically and chemically evaluated. All prototype formulations with the exception of the creams containing lidocaine HCl retained their initial physical and chemical stability properties after being stored at different conditions for one month. Based on the results generated at the 3-month time point, all prototypes with the exception of 2749-37 and 2749-38, qualify for further consideration. Prototype formulations 2749-37 and 2749-38 would require further optimization to address the phase separation observed at refrigerated conditions.

Example 2

In Vitro Percutaneous Absorption of Lidocaine from Prototype Formulations Using Human Skin Materials and Methods Based on the results of Example 1, eight prototype formulations were then selected and submitted for evaluation in an in vitro Skin Penetration Study. The purpose of this study was to characterize the in vitro percutaneous absorption of the actives (lidocaine free-base or lidocaine HCl) from prototype formulations, compared to two control formulations (a compounding pharmacy product and a marketed patch, LIDODERM®), following topical application to excised human skin from elective surgery. Selection of the formulas to test in this study was based primarily on physical and chemical stability, a desire to include a wide range of dosage forms (creams, spray-type, foam, and gels) containing either lidocaine base or lidocaine hydrochloride, and to obtain a broad range in the delivery from the prototype formulations.

This study was conducted using procedures adapted from the FDA and AAPS Report of the Workshop on Principles and Practices of In Vitro Percutaneous Penetration Studies: Relevance to Bioavailability and Bioequivalence. The clinically relevant dose of 5 mg/cm² was applied to dermatomed human abdominal tissue from a single donor obtained following elective surgery. The thickness of the tissue ranged from 0.025-0.038 inches (0.635-0.965 mm) with a mean+/−standard deviation in thickness of 0.031+/−0.004 inches (0.792+/−0.092 mm) and a coefficient of variation of 11.6%.

Percutaneous absorption was evaluated using this human abdominal tissue from a single donor, which was mounted in Bronaugh flow-through diffusion cells. The cells were maintained at a constant temperature of 32° C. by use of recirculating water baths. These cells have a nominal diffusion area of 0.64 cm². Fresh receptor phase, PBS with 0.1% sodium azide and 4% Bovine Serum Albumin, was continuously pumped under the tissue at a flow rate of nominally 1.0 ml/hr and collected in 6-hour intervals. The receptor phase samples were collected in pre-weighed scintillation vials; the post weights were taken following the study duration. Following the 24-hour duration exposure, the formulation residing on the tissue surface was removed by tape-stripping with CuDerm D-Squame stripping discs. The amount of Lidocaine residing in the epidermis, dermis, and receptor phase samples were properly labeled and were then sent to Pyxant Labs, Inc., an external contract bioanalytical laboratory, for subsequent analysis of Lidocaine content by LC/MS/MS and ultimate sample disposal.

Table 3 provides the composition of the formulations that were tested. The mass of Lidocaine per square centimeter of dosed tissue was calculated using the mass of Lidocaine in each sample divided by the area of skin exposed to the formulation.

Tissue permeation results were statistically evaluated using unpaired student's t-tests (significant differences between formulations were defined by a p-value of <0.05, at the 95% confidence interval).

Results

As shown in FIG. 1, Lidocaine delivery from all three gel (2749-30, 249-31, and 2749-32) candidates was equivalent or better than the compounding pharmacy formulation, and lidocaine delivery from two of the gels (2749-32 and 2749-30) was comparable to the LIDODERM® patch over a 24 hour period.

The LIDODERM® patch demonstrated a more linear rate of drug permeation over the 24 hour period compared to the test formulations. Formulations 2749-32 and 2749-30 delivered more lidocaine than all other formulations, including the LIDODERM® patch, from time of application to 6 hours. This indicates that these two formulations may have a faster onset of action and thus should provide more rapid pain relief.

Formulation 31 had comparable delivery profile to the compounding pharmacy cream. Prototype candidates containing Lidocaine HCl did not deliver as well as the formulations containing the free base.

Skin permeation (receptor phase levels) of Lidocaine ranged from 2.8 to 35 µg/cm² from Formulations 2749-72 and 2749-30, respectively. Formulations 2749-32 and 2749-30 had the highest permeation amount of Lidocaine with 34 and 35 µg/cm², respectively. Lidocaine delivery from Formulations 2749-32 and 2749-30 were comparable to the LIDODERM® patch, 34 µg/cm². Tissue permeation of Lidocaine from the control formulations (Compounding Pharmacy Product and Lidocaine Patch) was 24 and 34 µg/cm² (equivalent to 1.4 and 0.68 percent of the applied dose of Lidocaine), respectively. Cutaneous delivery of Lidocaine following 24 hours exposure from Formulations 2749-32 and 2749-30 was comparable to the Lidocaine Patch. Skin permeation of Lidocaine from Formulations 2749-32 and 2749-30 as well as the LIDODERM® patch was significantly higher (p<0.05, unpaired student's t-test) than the Compounding Pharmacy Product, 24 µg/cm². Skin permeation from Formulation 2749-31 (21 µg/cm²) was comparable to that of the Compounding Pharmacy Product.

The kinetic profile of tissue permeation is presented in FIG. 1 where the cumulative tissue permeation of Lidocaine in units of µg/cm² is plotted against time in hours. Skin permeation of Lidocaine was almost complete following the first 12 hours of exposure following topical application of the semisolid dosage forms; whereas, the LIDODERM® patch demonstrated a more linear rate of drug permeation over the 24 hour duration of this study. Formulations 2749-32 and 2749-30 delivered more Lidocaine that all other formulations from time of application to 6 hours, the first time point of receptor phase collection, suggesting that these two formulations may have a faster onset of action, which should results in more rapid pain relief. Formulation 2749-31 had comparable Lidocaine delivery profile to the Compounding Pharmacy Product. The tissue penetration of Lidocaine was statistically evaluated using unpaired student's t-tests (significant differences between formulations were defined by a p-value of <0.05, at the 95% confidence interval).

Results

The results are shown in FIG. 1 and Table 4. FIG. 1 is a graph of the cumulative penetration of lidocaine through human skin, measured as micrograms lidocaine/cm², over time in hours. Table 4 shows the cumulative receptor phase levels of lidocaine in percent of applied dose.

Lidocaine-containing gels exhibited greater cumulative penetration of lidocaine than lidocaine HCl-containing creams and sprays. LIDODERM®, a commercially available patch comprised of an adhesive material containing 5% lidocaine, which is applied to a non-woven polyester felt backing and covered with a polyethylene terephthalate (PET) film release liner, is applied only once for up to 12 hours in a given 24 hour period.

The Lidocaine Gel formulations 2749-32 and 2749-30 gave the highest levels of Lidocaine delivery of all semisolid dosage forms tested and the total amount of Lidocaine delivered over 24 hours from these two gel formulations was comparable to that achieved with the marketed LIDODERM® patch. Formulations 2749-32 and 2749-30 delivered more lidocaine than all other formulations, including the LIDODERM® patch, from time of application to 6 hours. This indicates that these two formulations may have a faster onset of action and thus should provide more rapid pain relief.

Comparable Lidocaine delivery and kinetic profile to the Compounding Pharmacy Product were achieved with Formulation 2749-31.

TABLE 3

Formulation Compositions

| Ingredients (% w/w) | Lidocaine Gel | | | Lidocaine HCl Gel | Spray-type | Foam | Creams | |
|---|---|---|---|---|---|---|---|---|
| | 2749-30 | 2749-31 | 2749-32 | 2749-28 | 2749-72 | 2749-52 | 2749-37 | 2749-38 |
| Lidocaine | 40 | 40 | 40 | | | | | |
| Lidocaine HCl | | | | 40 | 40 | 40 | 40 | 40 |
| Isopropyl Myristate | | | 10 | | | | | |
| TRANSCUTOL®P (diethyleneglycol monoethyl ether) | 10 | 20 | 10 | | | | | |
| Propylene glycol | 10 | 10 | 20 | | | | | |
| Dimethyl isosorbide | 10 | 10 | | | | | | |
| Ethyl acetate | 10 | | | | | | | |
| Isopropyl alcohol | 18.8 | | | 10 | | | | |
| Ethanol 200 proof | | 18.8 | 18.8 | | | | | |
| Hydroxypropyl cellulose, HXF Pharm | 1.2 | 1.2 | 1.2 | | | | | |
| Hydroxyethylcellulose, 250HHX Pharm | | | | 1 | 1 | | 0.5 | 0.5 |
| Benzyl Alcohol | | | | 2 | 2 | 2 | | |
| Propylene Glycol | | | | 10 | 10 | 5 | 5 | 5 |
| Glycerin | | | | | | 3 | | 2 |
| Sorbitol 70% | | | | 3 | | | | |
| Polysorbate 80 | | | | | 1 | | | |
| Sodium Laureth Sulfate | | | | | | 5 | | |
| Disodium Laureth Sulfosuccinate | | | | | | 5 | | |
| Diisopropyl Adipate | | | | | | | | 10 |
| White Petrolatum | | | | | | | 3 | |
| Light Mineral Oil | | | | | | | 10 | |
| Pemulen TR1 | | | | | | | 0.3 | 0.3 |
| Sorbitan Monoleate | | | | | | | 0.4 | 0.4 |
| Methylparaben | | | | | | | 0.17 | 0.17 |
| Propylparaben | | | | | | | 0.03 | 0.03 |
| Purified Water | | | | qsad | qsad | qsad | qsad | qsad |

TABLE 4

Cumulative Receptor Phase Levels of Lidocaine in Percent of Applied Dose

| | Formulation ID | | 0 | 6 | 12 | 18 | 24 |
|---|---|---|---|---|---|---|---|
| | | | | Hour(s) | | | |
| A) | ID: 2749-30 | Mean | 0 | 1.09 | 1.59 | 1.67 | 1.98 |
| | | SD | 0 | 0.25 | 0.17 | 0.18 | 0.46 |
| | | % CV | 0 | 22.95 | 10.94 | 10.88 | 23.46 |
| B) | ID: 2749-31 | Mean | 0 | 0.63 | 0.94 | 1.07 | 1.18 |
| | | SD | 0 | 0.30 | 0.49 | 0.47 | 0.46 |
| | | % CV | 0 | 47.53 | 51.74 | 44.26 | 39.04 |
| C) | ID: 2749-32 | Mean | 0 | 1.47 | 1.73 | 1.92 | 1.98 |
| | | SD | 0 | 0.37 | 0.38 | 0.42 | 0.44 |
| | | % CV | 0 | 25.08 | 21.96 | 22.03 | 22.36 |
| D) | ID: 2749-28 | Mean | 0 | 0.16 | 0.17 | 0.18 | 0.18 |
| | | SD | 0 | 0.13 | 0.13 | 0.13 | 0.13 |
| | | % CV | 0 | 78.68 | 77.71 | 73.03 | 72.28 |
| E) | ID: 2749-72 | Mean | 0 | 0.13 | 0.14 | 0.14 | 0.15 |
| | | SD | 0 | 0.05 | 0.05 | 0.05 | 0.05 |
| | | % CV | 0 | 35.20 | 36.06 | 35.99 | 35.30 |
| F) | ID: 2749-52 | Mean | 0 | 0.28 | 0.30 | 0.36 | 0.38 |
| | | SD | 0 | 0.15 | 0.16 | 0.20 | 0.21 |
| | | % CV | 0 | 53.25 | 53.58 | 54.70 | 54.20 |
| G) | ID: 2749-37 | Mean | 0 | 0.29 | 0.31 | 0.33 | 0.34 |
| | | SD | 0 | 0.23 | 0.24 | 0.26 | 0.26 |
| | | % CV | 0 | 79.61 | 77.82 | 77.47 | 76.29 |
| H) | ID: 2749-38 | Mean | 0 | 0.28 | 0.30 | 0.37 | 0.39 |
| | | SD | 0 | 0.19 | 0.19 | 0.22 | 0.22 |
| | | % CV | 0 | 67.57 | 63.34 | 59.77 | 57.39 |
| I) | ID: Compounding Pharmacy Product | Mean | 0 | 0.73 | 0.87 | 1.33 | 1.39 |
| | | SD | 0 | 0.14 | 0.15 | 0.17 | 0.14 |
| | | % CV | 0 | 18.92 | 17.46 | 12.76 | 10.40 |
| J) | ID: Lidocaine Patch | Mean | 0 | 0.24 | 0.34 | 0.62 | 0.68 |
| | | SD | 0 | 0.04 | 0.03 | 0.18 | 0.21 |
| | | % CV | 0 | 14.36 | 7.54 | 29.75 | 30.68 |

Example 3

Single Dose Dermal Irritation Study in New Zealand White Rabbits with Two Formulations of Lidocaine Gel, 40%

The objective of this study was to determine the potential toxicity and partial pharmacokinetic profile of two formulations of Lidocaine Gel, 40% following a single dermal application followed by a 14-day observation period.

The following test articles and gel vehicles were used in the study:
a. ARC-31 Lidocaine Gel, 40%
b. ARC-32 Lidocaine Gel, 40%
c. ARC-31 Lidocaine Gel Vehicle
d. ARC-32 Lidocaine Gel Vehicle ARC-31 and ARC-32 correspond to formulations 2749-31 and 2749-32 described above.

Groups (n/group/sex), test article, dose level (mg/kg) and dose weight (g/kg) are listed in Table 5:

TABLE 5

Summary of Test Paramaters

| Group Number | Number of Animals | | Test Article | Dose Level (mg/kg)[a] | Dose Weight (g/kg) |
|---|---|---|---|---|---|
| | Males | Females | | | |
| 1 | 3 | 3 | ARC-31 Lidocaine Gel Vehicle Control | Equivalent to Group 4 | Equivalent to Group 4 |
| 2 | 3 | 3 | ARC-31 Lidocaine Gel, 40% | 30 | 0.075 |

TABLE 5-continued

Summary of Test Paramaters

| Group Number | Number of Animals | | Test Article | Dose Level (mg/kg)[a] | Dose Weight (g/kg) |
|---|---|---|---|---|---|
| | Males | Females | | | |
| 3 | 3 | 3 | ARC-31 Lidocaine Gel, 40% | 300 | 0.75 |
| 4 | 3 | 3 | ARC-31 Lidocaine Gel, 40% | 1000 | 2.5 |
| 5 | 3 | 3 | ARC-32 Lidocaine Gel Vehicle Control | Equivalent to Group 8 | Equivalent to Group 8 |
| 6 | 3 | 3 | ARC-31 Lidocaine Gel, 40% | 30 | 0.075 |
| 7 | 3 | 3 | ARC-31 Lidocaine Gel, 40% | 300 | 0.75 |
| 8 | 3 | 3 | ARC-31 Lidocaine Gel, 40% | 1000 | 2.5 |

Animals

New Zealand white rabbits (24 male and 24 female, plus 4/sex alternates) were supplied by Charles River Laboratories and were 3-4 months of age on Study Day 1 (day of dosing). Males weighed between 2.7 and 3.3 kg and females weighed between 2.7 and 3.2 kg. Identification was by ear tag and color-coded cage card. The animals were acclimated for a minimum of 5 days prior to Study Day 1 and were acclimated to the Elizabethan collars at least once for at least 3 hours prior to Study Day 1. The animals were housed individually in stainless steel cages that conformed to standards set forth in the Animal Welfare Act (with all amendments) and the Guide for the Care and Use of Laboratory Animals (National Academy Press, Washington, D.C., 1996). Purina Certified Rabbit Diet # PMI 5325 was provided ad libitum 170 g per day after acclimation. Filtered tap water was provided ad libitum. Environmental controls were set to maintain temperatures of 16° C. to 22° C. with a relative humidity of 30% to 70%. A 12-hour light/12-hour dark cycle was maintained, except when interrupted to accommodate other study procedures. Ten or greater air changes per hour with 100% fresh air was maintained in the animal room.

Animals were randomly assigned to groups by a computerized weight-ordered distribution such that the group-mean body weights did not exceed ±10% of the overall mean weight for each sex at the time of randomization.

Administration of Test and Control Articles

The dose site on the dorsal back of the animals was clipped prior to randomization on Study Day −1 and as needed during the treatment period. Approximately 10% of the total body surface area was utilized for treatment application, using the following equation to determine total body surface area:

$$A \text{ (cm}^2\text{)} = 0.9 \times W^{2/3} \text{ (grams)}$$

where A=total body surface area and W=the total body weight.

Doses were applied to and spread evenly across the application sites at the appropriate dose weight with an allowance of ±10%. The exposure period was 6 hours±15 minutes. The animals wore Elizabethan collars during the exposure period to prevent contact with the control or test articles. Following the exposure period, any accumulation of control or test articles on the dose site was gently washed off with deionized water and gauze following the exposure period.

Toxicokinetic Sample Collection

Samples were collected on Study Day 1 at the following time-points: pre-dose, 1, 6, 8 and 24 hours post-dose. Blood (ca. 1.0 mL) was collected from a peripheral vessel; $K_2$EDTA was the anticoagulant. Samples were placed on ice following collection and centrifuged in a refrigerated centrifuge beginning within 30 minutes of collection. The plasma was transferred to storage tubes and frozen at −70° C. until shipped on dry ice by overnight courier for analysis.

Bioanalytical Method

Plasma concentrations of lidocaine were determined using a validated LC-MS/MS method. The lower limit of quantitation (LLOQ) and upper limit of quantitation (ULOQ) were 10 and 5000 ng/mL, respectively. Bioanalysis was conducted at Frontage Laboratories, Inc. (Malvern, Pa.). Bioanalytical data were captured using Analyst (version 1.4, Applied Biosystems) and Watson LIMS (version 7.3). Raw data are stored at the Central File of Frontage Laboratories, Inc. (Malvern, Pa.).

Toxicokinetic Calculations

Toxicokinetic calculations were performed using non-compartmental methods (WinNonlin, version 5.0.1, Pharsight Corporation, Mountain View, Calif.). Concentrations below the LLOQ were set to zero. $C_{max}$ and $T_{max}$ were the observed values for each animal. The linear trapezoidal method was used to determine the area under the concentration time curve. At least three time-points on the log-linear portion of the curve were needed to determine the elimination half-life (t½). $AUC_{0-inf}$ was not calculated for animals where t½ was not calculated. $AUC_{0-inf}$ was not calculated for animals in Group 6 since the percent of the extrapolated AUC from the last measurable concentration to infinity was greater than 30% of $AUC_{0-inf}$.

One of the male rabbits in Group 4 (No. 1461) that was administered 1000 mg lidocaine/kg died following the 6-hour sampling due to inadvertent oral exposure to the test article. It was replaced with Animal No. 1743. Plasma concentrations from Animal No. 1461 were not included in the calculations of the mean values.

Results

The mean plasma concentrations of lidocaine are presented in Table 6 are displayed in FIGS. 2 (ARC-31) and 3 (ARC-32). The mean pharmacokinetic parameters are in Table 8. $AUC_{0-t}$ and $C_{max}$ versus dose are displayed in FIGS. 4 and 5.

TABLE 6

Mean plasma concentration of lidocaine in White New Zealand Rabbits

| Group/Dose[a] | Sex | Statistic | 0.0 | 1.0 | 6.0 | 8.0 | 24.0 |
|---|---|---|---|---|---|---|---|
| | | | | Time (hr post-dose) | | | |
| 1/Control | Male | Mean | 0.000[b] | 0.000 | 0.000 | 0.000 | 25.347 |
| | | SD | 0.000 | 0.000 | 0.000 | 0.000 | 43.903 |
| | | CV % | NC | NC | NC | NC | 173.2 |
| | Female | Mean | 0.000 | 16.227 | 6.595 | 100.742 | 0.000 |
| | | SD | 0.000 | 28.105 | 11.422 | 68.719 | 0.000 |
| | | CV % | NC | 173.2 | 173.2 | 68.2 | NC |
| 2/30 mg/kg | Male | Mean | 0.000 | 21.279 | 40.787 | 83.546 | 0.000 |
| | | SD | 0.000 | 8.904 | 6.560 | 30.794 | 0.000 |
| | | CV % | NC | 41.8 | 16.1 | 36.9 | NC |
| | Female | Mean | 0.000 | 33.027 | 53.649 | 166.753 | 0.000 |
| | | SD | 0.000 | 25.871 | 10.030 | 14.416 | 0.000 |
| | | CV % | NC | 78.3 | 18.7 | 8.6 | NC |
| 3/300 mg/kg | Male | Mean | 0.000 | 188.057 | 670.756 | 1626.184 | 84.630 |
| | | SD | 0.000 | 103.981 | 117.289 | 672.459 | 3.960 |
| | | CV % | NC | 55.3 | 17.5 | 41.4 | 4.7 |
| | Female | Mean | 0.000 | 245.736 | 475.202 | 1726.581 | 79.099 |
| | | SD | 0.000 | 136.110 | 117.717 | 426.354 | 39.989 |
| | | CV % | NC | 55.4 | 24.8 | 24.7 | 50.6 |
| 4/1000 mg/kg | Male | Mean | 0.000 | 293.497 | 1406.016 | 2253.274 | 662.739 |
| | | SD | 0.000 | 119.690 | 920.218 | 854.830 | 431.862 |
| | | CV % | NC | 40.8 | 65.4 | 37.9 | 65.2 |
| | Female | Mean | 0.000 | 717.264 | 2695.865 | 2979.010 | 398.799 |
| | | SD | 0.000 | 119.922 | 739.884 | 532.547 | 131.243 |
| | | CV % | NC | 16.7 | 27.4 | 17.9 | 32.9 |
| 5/Control | Male | Mean | 0.000[b] | 0.000 | 15.566 | 20.335 | 0.000 |
| | | SD | 0.000 | 0.000 | 26.961 | 35.221 | 0.000 |
| | | CV % | NC | NC | 173.2 | 173.2 | NC |
| | Female | Mean | 0.000 | 77.219 | 51.693 | 71.884 | 6.060 |
| | | SD | 0.000 | 133.747 | 58.869 | 80.646 | 10.496 |
| | | CV % | NC | 173.2 | 113.9 | 112.2 | 173.2 |
| 6/30 mg/kg | Male | Mean | 0.000 | 617.700 | 326.977 | 273.412 | 0.000 |
| | | SD | 0.000 | 103.203 | 35.797 | 39.155 | 0.000 |
| | | CV % | NC | 16.7 | 10.9 | 14.3 | NC |
| | Female | Mean | 0.000 | 412.280 | 207.944 | 215.558 | 0.000 |
| | | SD | 0.000 | 139.137 | 79.411 | 103.212 | 0.000 |
| | | CV % | NC | 33.7 | 38.2 | 47.9 | NC |
| 7/300 mg/kg | Male | Mean | 0.000 | 4719.600 | 3589.358 | 2970.820 | 29.451 |
| | | SD | 0.000 | 1760.730 | 622.011 | 1217.017 | 5.689 |
| | | CV % | NC | 37.3 | 17.3 | 41.0 | 19.3 |
| | Female | Mean | 0.000 | 3019.929 | 2432.354 | 2207.219 | 48.963 |
| | | SD | 0.000 | 1026.264 | 114.250 | 291.666 | 26.217 |
| | | CV % | NC | 34.0 | 4.7 | 13.2 | 53.5 |

[a] n = 3/sex/group
[b] Less than LLOQ (10 ng/mL)
NC: Not calculated

TABLE 7

Mean pharmacokinetic parameters for lidocaine in White New Zealand Rabbits

| Group/Dose[a] | Sex | Statistic | $C_{max}$ (ng/mL) | $T_{max}$[b] (hr) | $t_{1/2}$ (hr) | $AUC_{0-t}$ (ng · hr/mL) | $AUC_{0-inf}$ (ng · hr/mL) |
|---|---|---|---|---|---|---|---|
| 1/Control | Male | Mean | 25.347 | NC | NC | 202.779 | NC |
| | | SD | 43.903 | NC | NC | 351.223 | NC |
| | | CV % | 173.2 | | NC | 173.2 | NC |
| | Female | Mean | 107.984 | 8.0 | NC | 172.503 | NC |
| | | SD | 57.241 | (1.0-8.0) | NC | 59.899 | NC |
| | | CV % | 53.0 | | NC | 34.7 | NC |
| 2/30 mg/kg | Male | Mean | 83.546 | 8.0 | NC | 290.137 | NC |
| | | SD | 30.794 | (8.0-8.0) | NC | 41.834 | NC |
| | | CV % | 36.9 | | NC | 14.4 | NC |
| | Female | Mean | 166.753 | 8.0 | NC | 453.608 | NC |
| | | SD | 14.416 | (8.0-8.0) | NC | 126.719 | NC |
| | | CV % | 8.6 | | NC | 27.9 | NC |

TABLE 7-continued

Mean pharmacokinetic parameters for lidocaine in White New Zealand Rabbits

| Group/Dose[a] | Sex | Statistic | $C_{max}$ (ng/mL) | $T_{max}$[b] (hr) | $t^{1/2}$ (hr) | $AUC_{0-t}$ (ng·hr/mL) | $AUC_{0-inf}$ (ng·hr/mL) |
|---|---|---|---|---|---|---|---|
| 3/300 mg/kg | Male | Mean | 1626.184 | 8.0 | NC | 18224.512 | NC |
| | | SD | 672.459 | (8.0-8.0) | NC | 6404.324 | NC |
| | | CV % | 41.4 | | NC | 35.1 | NC |
| | Female | Mean | 1726.581 | 8.0 | NC | 18572.436 | NC |
| | | SD | 426.354 | (8.0-8.0) | NC | 4071.059 | NC |
| | | CV % | 24.7 | | NC | 21.9 | NC |
| 4/1000 mg/kg | Male | Mean | 2253.274 | 8.0 | NC | 31382.922 | NC |
| | | SD | 854.830 | (8.0-8.0) | NC | 12391.781 | NC |
| | | CV % | 37.9 | | NC | 39.5 | NC |
| | Female | Mean | 3336.581 | 8.0 | NC | 41588.798 | NC |
| | | SD | 295.536 | (6.0-8.0) | NC | 1837.924 | NC |
| | | CV % | 8.9 | | NC | 4.4 | NC |
| 5/Control | Male | Mean | 20.335 | NC | NC | 74.816 | NC |
| | | SD | 35.221 | NC | NC | 129.585 | NC |
| | | CV % | 173.2 | | NC | 173.2 | NC |
| | Female | Mean | 94.372 | 8.0 | NC | 970.790 | NC |
| | | SD | 119.367 | (1.0-8.0) | NC | 1528.680 | NC |
| | | CV % | 126.5 | | NC | 157.5 | NC |
| 6/30 mg/kg | Male | Mean | 617.700 | 1.0 | 6.6 | 3270.930 | NC |
| | | SD | 103.203 | (1.0-1.0) | 2.8 | 268.450 | NC |
| | | CV % | 16.7 | | 43.3 | 8.2 | NC |
| | Female | Mean | 412.280 | 1.0 | 6.7 | 2180.202 | NC |
| | | SD | 139.137 | (1.0-1.0) | 1.2 | 796.028 | NC |
| | | CV % | 33.7 | | 18.2 | 36.5 | NC |
| 7/300 mg/kg | Male | Mean | 4719.600 | 1.0 | 2.5 | 53694.539 | 53802.526 |
| | | SD | 1760.730 | (1.0-1.0) | 0.1 | 17681.112 | 17682.226 |
| | | CV % | 37.3 | | 5.9 | 32.9 | 32.9 |
| | Female | Mean | 3178.373 | 1.0 | 3.1 | 37829.709 | 38057.218 |
| | | SD | 773.649 | (1.0-6.0) | 0.5 | 5436.960 | 5311.303 |
| | | CV % | 24.3 | | 15.2 | 14.4 | 14.0 |

[a] n = 3/sex/group
[b] Median and range of $T_{max}$
NC: Not calculated

Measurable concentrations of lidocaine above the LLOQ (10 ng/mL) were detected in 16 of 60 plasma samples collected from animals that received only the vehicle. Six of these animals were administered the ARC-31 vehicle and ten received the ARC-32 vehicle. Values ranged from two to 23 times the LLOQ. When the control samples with measurable concentrations were reassayed, the concentrations were not different from the initial results, based on the SOP for the reanalysis of samples. None of the samples collected pre-dose contained measurable concentrations of lidocaine.

ARC-31 Lidocaine Gel

Figure 2A:
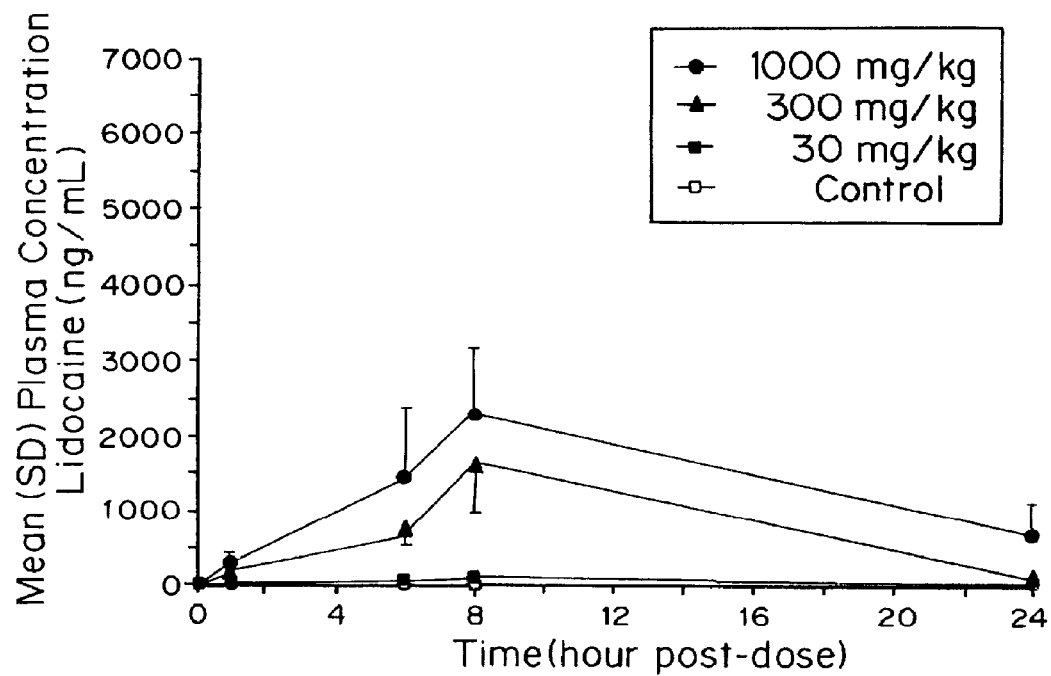
FIG. 2A show the mean plasma concentration in male rabbits and FIG. 2B shows the mean plasma concentration in female rabbits.

The mean $C_{max}$ of lidocaine in male rabbits administered the compound dermally in the ARC-31 gel increased from 83.546 to 1626.184 ng/mL when the dose increased from 30 (Group 2) to 300 mg/kg (Group 3), a 19-fold increase (Table 6, FIG. 2A). Increasing the dose further to 1000 mg/kg (Group 4) increased $C_{max}$ only 1.4-fold to 2253.274 ng/mL. $AUC_{0-t}$ was also disproportionately greater (63-fold) when the dose increased from 30 to 300 mg, averaging 290.137 ng·hr/mL at the lower dose and 18224.512 ng·hr/mL at the higher dose. Like $C_{max}$, $AUC_{0-t}$ increased only 1.7-fold (31382.922 ng·hr/mL) when the dose increased from 300 to 1000 mg/kg. The median $T_{max}$ occurred at 8 hours post-dose at all three dose levels.

Figure 2B:
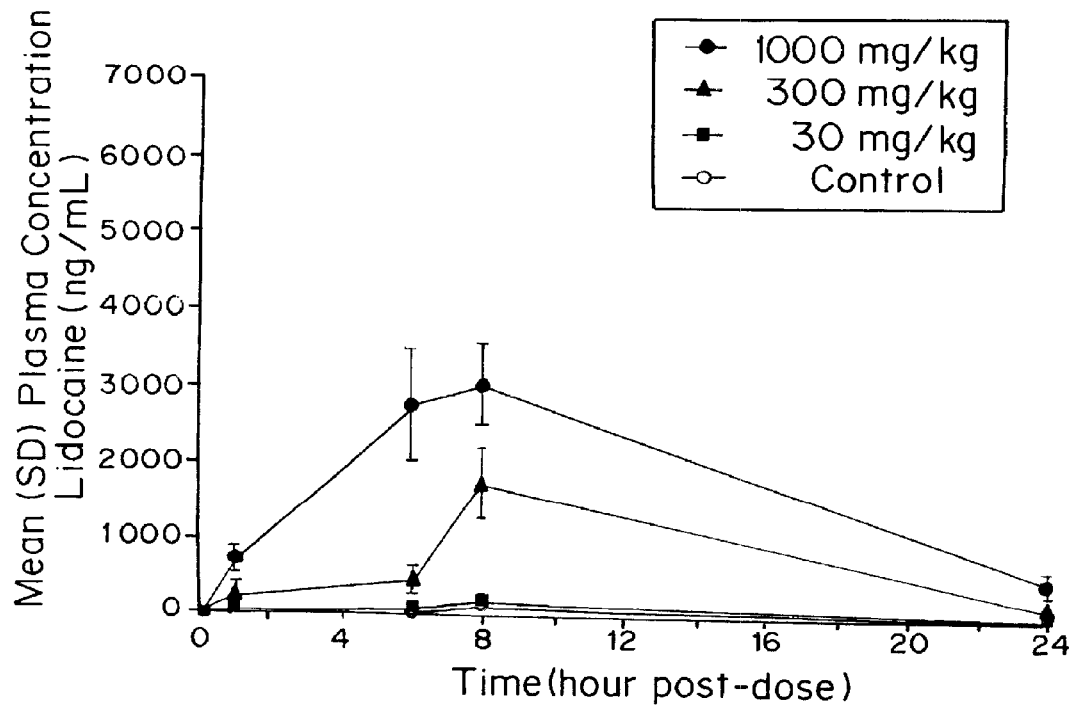

In female rabbits, the mean $C_{max}$ of lidocaine increased ten-fold from 166.753 to 1726.581 ng/mL when the dermal dose increased from 30 to 300 mg/kg (Table 6, FIG. 2B). It increased approximately two-fold to 3336.581 ng/mL when the dose increased to 1000 mg/kg (Table 6). The mean value of $AUC_{0-t}$, though, increased 41-fold when the dose increased from 30 to 300 mg/kg (453.608 and 18572.436 ng·hr/mL, respectively) (Table 7, FIG. 5). $AUC_{0-t}$ increased approximately two-fold as the dose was increased to 1000 mg/kg (41588.798 ng·hr/mL) (Table 7). The median $T_{max}$ was 8 hours post-dose at all three dose levels.

The elimination half-life was measurable in only one animal at the 1000 mg/kg dose level; it was 5.9 hours in female Animal Number 1458. Mean values of $C_{max}$ and $AUC_{0-t}$ in male and female rabbits were comparable at all 3 dose levels.

ARC-32 Lidocaine Gel

Figure 3A:
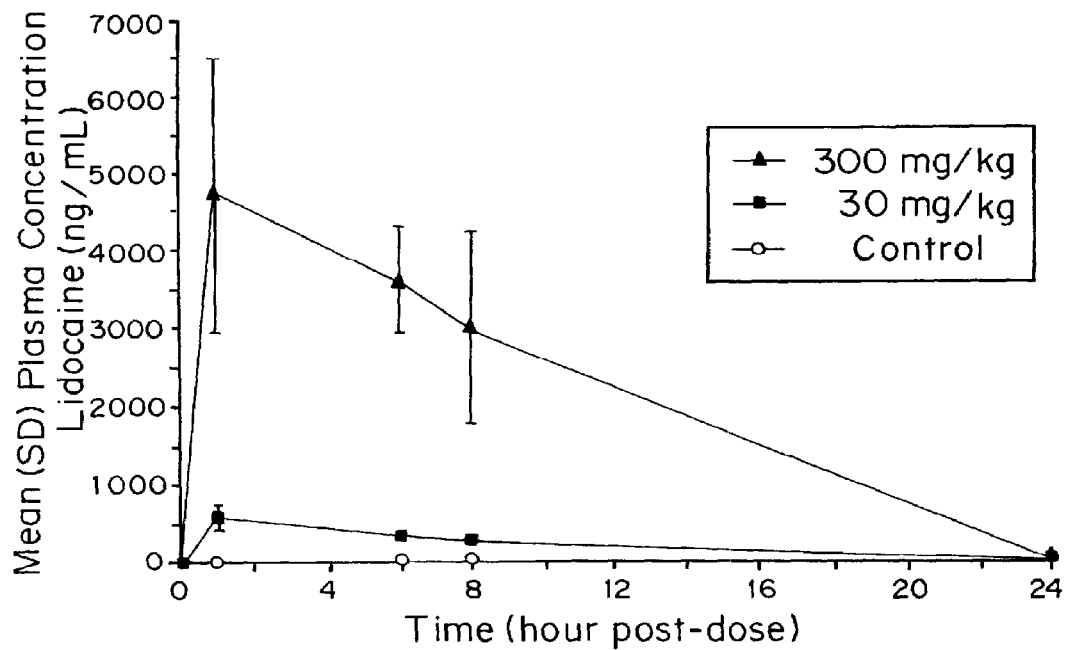
FIG. 3A show the mean plasma concentration in male rabbits and FIG. 3B shows the mean plasma concentration in female rabbits.

The mean $C_{max}$ value of lidocaine in male rabbits increased 7.6-fold when the dose in the ARC-32 lidocaine gel increased from 30 to 300 mg/kg (617.700 and 4719.600 ng/mL, respectively) (Table 7, FIG. 3A). The mean AUC0-t increased disproportionately from 3270.930 to 53694.539 ng·hr/mL, a 16-fold increase (Table 7). The median $T_{max}$ occurred at 1 hour post-dose, the first sample time-point, for all 3 doses. The mean t½ value at the 30 mg/kg dose was 6.6 hours and 2.5 hours at the 300 mg/kg dose (Table 7).

Figure 3B:
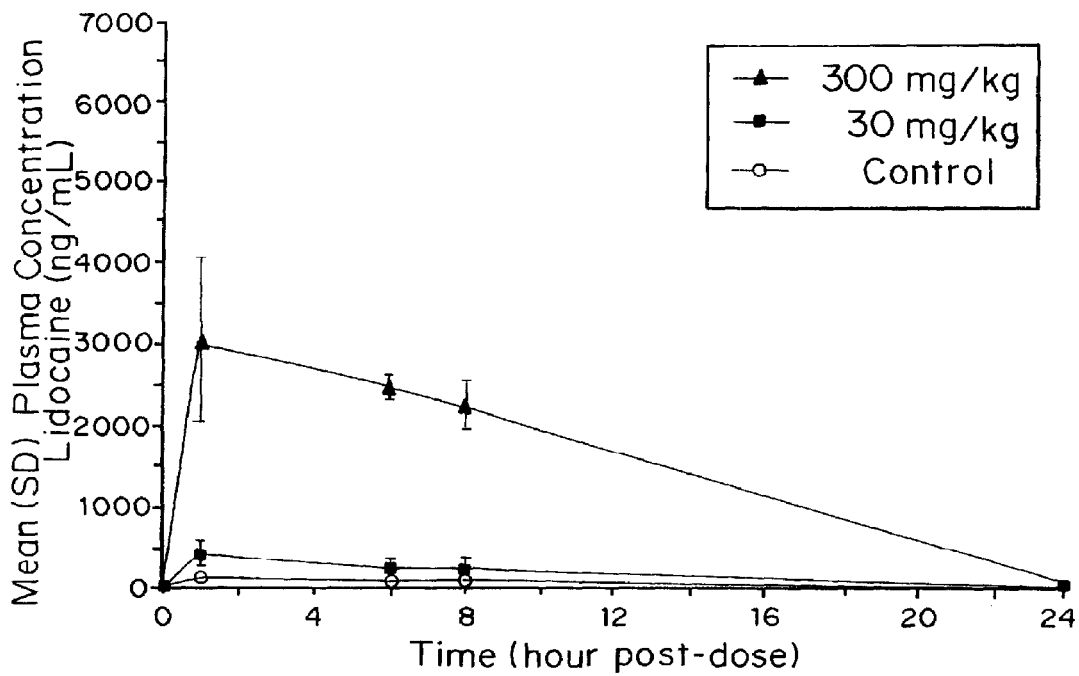

In female rabbits, the mean $C_{max}$ value increased 7.7-fold as the dose increased from 30 to 300 mg/kg (412.280 and 3178.373 ng/mL, respectively) (Table 7, FIG. 3B). The mean value of $AUC_{0-t}$ increased 17-fold when the dose increased ten-fold from 30 to 300 mg/kg (2180.202 and 37829.709 ng·hr/mL, respectively). The mean t½ values at the 30 and 300 mg/kg dose levels were 6.7 hours and 3.1 hours, respectively.

The mean $C_{max}$ and $AUC_{0-t}$ values were slightly higher in male versus female rabbits (FIGS. 4 and 5), but the increase was only 42-50% greater at the 30 and 300 mg/kg dose levels. Mean $T_{max}$ and t½ values were comparable between the two sexes.

Values for $AUC_{0-inf}$ could be calculated only in the rabbits dosed at 300 mg/kg with the ARC-32 lidocaine gel. The mean values were less than 1% greater than $AUC_{0-t}$.

Samples from male and female rabbits dosed at 1000 mg/kg with the ARC-32 lidocaine gel (Group 8) were collected only at pre-dose and 1 hour post-dose as all of the animals were either moribund or dead at 6 hours post-dose. At 1 hour post-dose, the mean concentration in male rabbits was 13201.466 ng/mL and 15709.008 ng/mL in females. These values are approximately 3- to 4-fold higher than in rabbits dosed at 300 mg/kg. Plasma samples were collected from one female and two male rabbits that were moribund; lidocaine concentrations ranged from approximately 12,000 to 25,600 ng/mL.

Comparison of ARC-31 and ARC-32 Lidocaine Gels

Exposure to lidocaine, as measured by both $C_{max}$ and $AUC_{0-t}$, was higher when the test article was delivered using the ARC-32 gel compared to the ARC-31 gel formulation.

Figure 4:
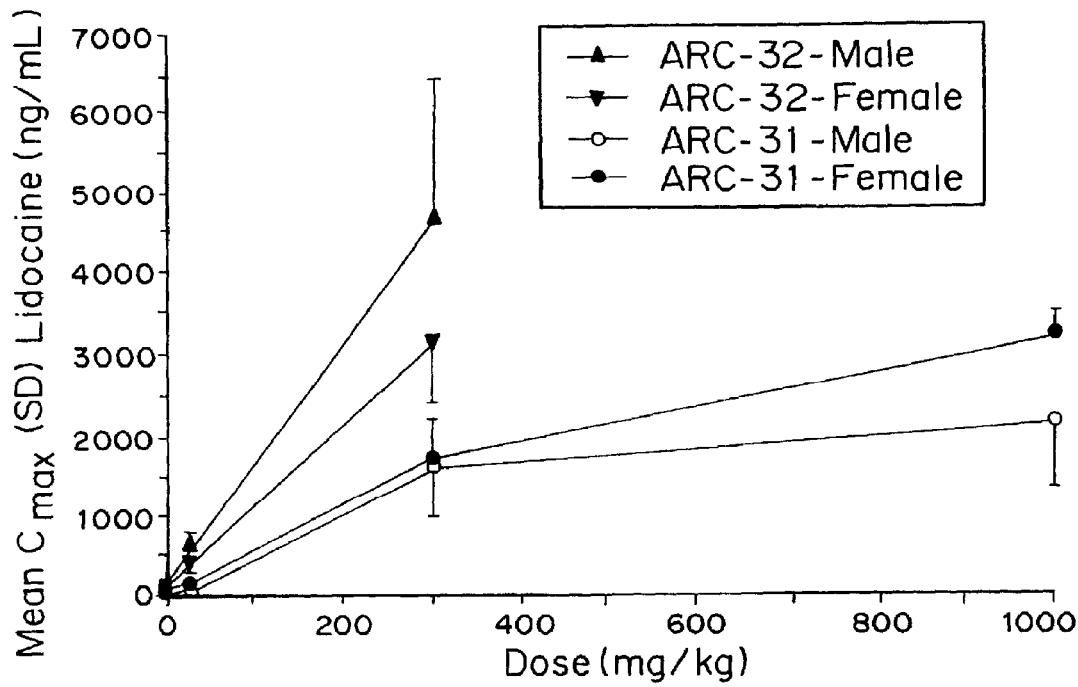
FIG. 4 is a graph showing the mean $C_{max}$ (ng/ml) as a function of dose of lidocaine (mg/kg) in White New Zealand Rabbits administered ARC-31 (male rabbits, ○; females rabbits, ●) and ARC-32 (male rabbits, ▲; female rabbits, ▼).
Figure 5:
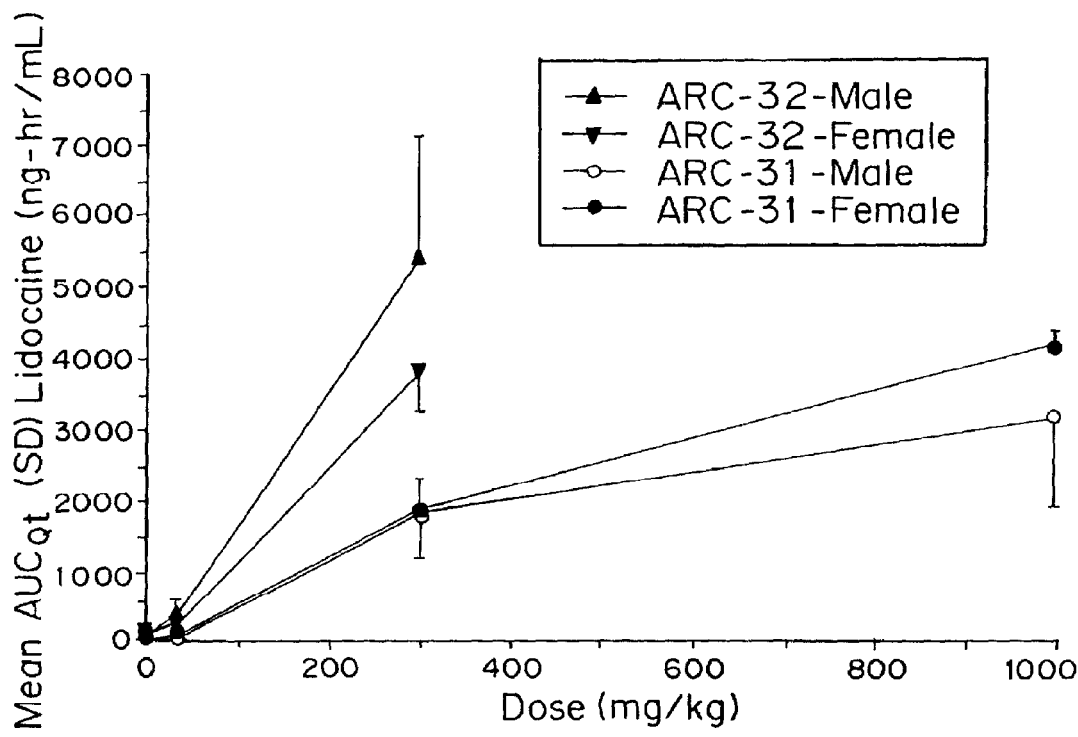
FIG. 5 is a graph showing the mean $AUC_{0-t}$ (ng*hr/ml) as a function of dose of lidocaine (mg/kg) in White New Zealand Rabbits administered ARC-31 (male rabbits, ○; females rabbits, ●) and ARC-32 (male rabbits, ▲; female rabbits, ▼).

In male rabbits, the $C_{max}$ of lidocaine was seven-fold higher for the ARC-32 gel compared to the ARC-31 gel at the 30 mg/kg dose (617.700 and 83.546 ng/mL, respectively) and approximately three-fold at the 300 mg/kg dose level (4719.600 and 1626.184 ng/mL) (FIG. 4). $AUC_{0-t}$ was eleven-fold higher at the 30 mg/kg dose (3270.930 and 290.137 ng·hr/mL) and three-fold higher at the 300 mg/kg dose level (53694.539 and 18224.512 ng·hr/mL) when lidocaine was delivered using the ARC-32 gel compared to the ARC-31 gel (FIG. 5).

In female rabbits, the $C_{max}$ of lidocaine was 2.5-fold higher when the ARC-32 gel was used compared to the ARC-31 gel at the 30 mg/kg dose (412.280 and 166.753 ng/mL, respectively) and almost two-fold at the 300 mg/kg dose (3178.373 and 1726.581 ng/mL) (FIG. 4). $AUC_{0-t}$ was approximately five-fold higher at the 30 mg/kg dose (2180.202 and 453.608 ng·hr/mL) and two-fold higher at the 300 mg/kg dose (37829.709 and 18572.436 ng·hr/mL) when lidocaine was delivered using the ARC-32 gel compared to the ARC-31 gel (FIG. 5).

Conclusions $AUC_{0-t}$ increased disproportionately in male and female rabbits when the dermal dose was increased from 30 to 300 mg/kg when lidocaine was delivered using either the ARC-31 or ARC-32 lidocaine gel, 40% formulation. It increased 1.7- to two-fold in male and female rabbits when the dose of the ARC-31 gel was increased to 1000 mg/kg.

$C_{max}$ increased approximately 7- to 19-fold when the dose increased from 30 to 300 mg/kg using either gel.

The median $T_{max}$ of lidocaine was 8 hours when the rabbits were dosed with the ARC-31 lidocaine gel; it decreased to 1 hour when the ARC-32 lidocaine gel was used.

The mean values of $C_{max}$ and $AUC_{0-t}$ of lidocaine between male and female animals were either comparable when the ARC-31 gel was dosed or 42-50% higher in males when the ARC-32 gel was administered.

Exposure to lidocaine, as measured using both $C_{max}$ and $AUC_{0-t}$, was greater in rabbits dosed using the ARC-32 lidocaine gel compared to the ARC-31 lidocaine gel.

Example 4

Biocompatibility Study in New Zealand White Rabbits with Two Formulations of Lidocaine Gel, 40%

A biocompatibility study of two lidocaine gel formulations containing 40% lidocaine was conducted. The study was conducted as described in Example 3.

Animals were dosed once via dermal application to the dorsal back. Parameters evaluated during this study were clinical observations, dermal scores, body weights, physical examinations, toxicokinetic evaluation, macroscopic evaluation of the tissues, and organ weights.

For ARC-31 Lidocaine Gel 40%, one male at 1000 mg/kg died on Study Day 1 soon after the six-hour exposure period. No other animals receiving ARC-31 Lidocaine Gel 40% had similar findings. Due to the fact that the onset of these clinical observations was relatively soon after the exposure period, it is likely that the animal may have ingested some of the residual test article which resulted in the animal's death. This animal was replaced on study. At necropsy, red skin on the back had persisted and was noted for this Group 4 male. No other animals that received the single dermal application of ARC-31 Lidocaine Gel 40% showed any test article-related findings through the termination of the study on Study Day 4.

For ARC-32 Lidocaine Gel 40%, all six animals receiving 1000 mg/kg died early or were euthanized as moribund on Study Day 1. At approximately 60 to 90 minutes following the application of ARC-32, animals at 300 mg/kg and 1000 mg/kg were observed with neurological-related signs of abnormal gait, decreased activity, convulsions, loss of righting reflex, labored breathing, gasping, rales, and/or increased salivation and the exposure period for these animals was terminated. Following removal of the test article, animals at 1000 mg/kg did not appear to be recovering and were euthanized or died; animals at 300 mg/kg did show signs of recovery and remained on study.

Additionally, redness of the back/application site was noted in five of six animals receiving the ARC-32 vehicle control and five of six animals at 300 mg/kg ARC-32. This redness was typically seen on Study Days 2, 3, and 4 and was correlated by dermal scores of very slight to severe erythema. Because the redness was seen in the vehicle control group, it is likely that the vehicle control or the amount of vehicle control applied was partially responsible for the redness noted at 300 mg/kg; only two of six animals at 30 mg/kg ARC-32 had redness. Swelling of the back was also noted in animals at 300 mg/kg ARC-32 and correlated to very slight edema noted on Study Days 2, 3, and 4.

All animals at 1000 mg/kg ARC-32 and one male at 300 mg/kg ARC-32 had red discoloration of the treated skin that was collected from the application site at necropsy. Organ weights were not affected by administration of either of the test articles.

We claim:

1. A method of treating pain comprising topically administering an effective amount of a formulation for treating pain to a site in need thereof,
    wherein the formulation comprises a local anesthetic in a gel,
    wherein the local anesthetic is present in the gel in an amount from 40% by weight up to 60% by weight of the formulation,
    wherein the local anesthetic comprises a free base caine alkaloid, and an effective amount of the free base caine alkaloid local anesthetic is released into the skin to provide pain relief at or near the site of administration without systemic toxicity for at least three hours.

2. The method of claim 1 wherein the local anesthetic is selected from the group consisting of dibucaine, bupivacaine, etidocaine, tetracaine, lidocaine, and xylocalne.

3. The method of claim 2 wherein the local anesthetic is lidocaine.

4. The method of claim 1 wherein the local anesthetic is present in an amount of approximately 40% by weight.

5. The method of claim 1 providing an initial burst release within two hours of administration.

6. The method of claim 1 providing an initial burst release within four hours of administration.

7. The method of claim 1 providing an initial burst release within six hours of administration.

8. The method of claim 1 providing an initial burst release within eight hours of administration.

9. The method of claim 1 providing an initial burst release within twelve hours of administration.

10. The method of claim 1 wherein the concentration of the local anesthetic is sufficiently high that release is not governed by simple diffusion.

11. The method of claim 1 wherein the formulation is administered to wounds, abrasions, or burns.

12. The method of claim 1 wherein the formulation is administered to a site prior to a needle insertion or other medical procedure.

13. The method of claim 1 wherein the formulation is administered to a site prior to a cosmetic procedure.

14. The method of claim 13 wherein the cosmetic procedure is removal of hair.

15. The method of claim 1 wherein the formulation is administered to a child.

16. The method of claim 1 wherein the formulation is administered to an animal.

17. The method of claim 1 wherein the formulation comprises one or more excipients selected from the group consisting of isopropyl myristate, a permeation enhancer, propylene glycol, dimethyl isosorbide, ethanol, hydroxypropyl cellulose, hydroxyethyl cellulose, benzyl alcohol and sorbitol.

18. The method of claim 17, wherein the permeation enhancer is diethyleneglycol monoethyl ether.

19. The method of claim 18, wherein the formulation comprises diethyleneglycol monoethyl ether, propylene glycol, ethanol, and hydroxypropyl cellulose.

20. The method of claim 19, wherein the formulation further comprises isopropyl myristate or dimethyl isosorbide.

21. The method of claim 17, wherein the local anesthetic is present in an amount of about 40% by weight.

22. The method of claim 20, wherein the local anesthetic is present in an amount of about 40% by weight.

23. The method of claim 21, wherein the formulation comprises about 40% by weight lidocaine free base, about 10% by weight diethyleneglycol monoethyl ether, about 10% by weight propylene glycol, about 10% by weight dimethyl isosorbide, about 10% by weight ethyl acetate, about 18.8% by weight isopropyl alcohol, and about 1.2% by weight hydroxypropyl cellulose.

24. The method of claim 22, wherein the formulation comprises about 40% by weight lidocaine free base, about 10% by weight diethyleneglycol monoethyl ether, about 20% by weight propylene glycol, about 18.8% by weight ethanol, and about 1.2% by weight hydroxypropyl cellulose.

* * * * *